United States Patent
Lu et al.

(10) Patent No.: US 10,930,371 B2
(45) Date of Patent: Feb. 23, 2021

(54) METHOD OF CREATING CHARACTERISTIC PEAK PROFILES OF MASS SPECTRA AND IDENTIFICATION MODEL FOR ANALYZING AND IDENTIFYING MICROORGANIZM

(71) Applicants: Jang-Jih Lu, Taipei (TW); Chun-Hsien Chen, Taoyuan (TW); Hsin-Yao Wang, Chiayi (TW); Tsui-Ping Liu, New Taipei (TW)

(72) Inventors: Jang-Jih Lu, Taipei (TW); Chun-Hsien Chen, Taoyuan (TW); Hsin-Yao Wang, Chiayi (TW); Tsui-Ping Liu, New Taipei (TW)

(73) Assignees: CHANG GUNG MEMORIAL HOSPITAL, LINKOU, Taoyuan (TW); CHANG GUNG UNIVERSITY, Taoyuan (TW)

( * ) Notice: Subject to any disclaimer, the term of this patent is extended or adjusted under 35 U.S.C. 154(b) by 889 days.

(21) Appl. No.: 15/644,886

(22) Filed: Jul. 10, 2017

(65) Prior Publication Data
US 2019/0012430 A1 Jan. 10, 2019

(51) Int. Cl.
*G16B 40/00* (2019.01)
*G06N 7/00* (2006.01)
(Continued)

(52) U.S. Cl.
CPC .............. *G16B 40/00* (2019.02); *G06N 7/005* (2013.01); *G16B 40/10* (2019.02); *G06N 20/00* (2019.01)

(58) Field of Classification Search
CPC ........ G16B 40/00; G16B 40/10; G06N 7/005; G06N 20/00; G06F 19/24
(Continued)

(56) References Cited

U.S. PATENT DOCUMENTS

2013/0325771 A1* 12/2013 Paauw ................... G16C 20/70
706/20
2014/0343864 A1* 11/2014 Strubel .............. G06K 9/00147
702/19
(Continued)

OTHER PUBLICATIONS

De Bruyne et al., "Bacterial species identification from MALDI-TOF mass spectra through data analysis and machine learning", Systematic and Applied Microbiology 34 (2011) 20-29. (Year: 2011).*
Vervier et al., "Benchmark of structured machine learning methods for microbial identification from mass-spectrometry data", Jun. 25, 2015. (Year: 2015).*
(Continued)

*Primary Examiner* — Dave Misir

(57) ABSTRACT

A method of creating characteristic peak profiles of mass spectra and identification model for analyzing and identifying microorganisms are provided. MALDI-TOF MS data of microorganisms having the same feature are gathered. Discretization of the data is performed. Density-based clustering is used to find m/z values of spectral peaks with high probability of occurrence from the discretized data. A characteristic MS peak profile is created for every specific feature of microorganisms. Every such a characteristic profile forms a feature template. The mass spectrum of each known isolate is matched against all the feature templates and a number of matched vectors are obtained. The matched vectors are then concatenated into a single "integrated vector." Then, a machine learning method and the integrated vectors generated from all known isolates are used to create a classification model for microorganism identification.

4 Claims, 7 Drawing Sheets

(51) Int. Cl.
*G16B 40/10* (2019.01)
*G06N 20/00* (2019.01)

(58) Field of Classification Search
USPC .......................................................... 706/12
See application file for complete search history.

(56) References Cited

U.S. PATENT DOCUMENTS

| 2015/0051840 | A1* | 2/2015 | Vervier | G06K 9/00147 |
| | | | | 702/19 |
| 2016/0350475 | A1* | 12/2016 | Vestal | G16B 35/00 |
| 2016/0371430 | A1* | 12/2016 | Mahe | G16B 40/00 |
| 2019/0049445 | A1* | 2/2019 | Arsac | G01N 33/56911 |

OTHER PUBLICATIONS

Timm et al., "Peak intensity prediction in MALDI-TOF mass spectrometry: A machine learning study to support quantitative proteonnics", BMC Bioinformatics 2008. (Year: 2008).*

Calderaro et al., "Identification of Borrelia Species after Creation of an In- House MALDI-TOF MS Database", PLOS ONE, Feb. 2014. (Year: 2014).*

Al Masoud et al., "Optimization of matrix assisted desorption/ ionization time of flight mass spectrometry (MALDI-TOF-MS) for the characterization of *Bacillus* and *Brevibacillus* species", Analytica Chimica Acta 840 (2014) 49-57. (Year: 2014).*

Marklein et al., "Matrix-Assisted Laser Desorption Ionization—Time of Flight Mass Spectrometry for Fast and Reliable Identification of Clinical Yeast Isolates", Journal of Clinical Microbiology, Sep. 2009, p. 2912-2917. (Year: 2009).*

* cited by examiner

| sub-species A | 1276.889 | 1505.849 | 1934.423 | 2066.205 | 2081.884 | 2149.891 | 2241.782 | 2411.518 | 2428.76 | 2428.983 | 2450.723 | ... |
|---|---|---|---|---|---|---|---|---|---|---|---|---|
| sub-species B | 3209.517 | 3421.267 | 3443.756 | 3783.209 | 4045.327 | 4304.756 | 4445.612 | 4589.75 | 4813.485 | 5031.712 | 5052.251 | ... |
| sub-species C | 5302.261 | 5523.849 | 5524.064 | 6421.607 | 6550.355 | 6612.033 | 6815.52 | 6815.717 | 6841.991 | 6886.65 | 7564.775 | ... |

FIG.3

| | matched against the feature template of sub-species A (Vector 1) | | | | matched against the feature template of sub-species B (Vector 2) | | | | matched against the feature template of sub-species C (Vector 3) | | | |
|---|---|---|---|---|---|---|---|---|---|---|---|---|
| integrated vector | ...... | 0 | 1 | 0 | 0 | 0 | ...... | 1 | 1 | 0 | 1 | 0 | 1 | 1 | 0 | ...... |

FIG.4

|  | ST 5 | | ST 45 | | ST 59 | | ST 239 | |
| --- | --- | --- | --- | --- | --- | --- | --- | --- |
|  | average | standard deviation | average | standard deviation | average | standard deviation | average | standard deviation |
| DT | 0.861 | 5.03E-02 | 0.603 | 1.32E-01 | 0.906 | 4.77E-02 | 0.962 | 2.27E-02 |
| SVM | 0.953 | 2.40E-02 | 0.958 | 2.63E-02 | 0.989 | 6.78E-03 | 0.9946 | 5.41E-03 |
| KNN | 0.909 | 3.76E-02 | 0.919 | 7.03E-02 | 0.978 | 2.19E-02 | 0.957 | 2.09E-02 |

FIG.6

| machine learning methods | accuracy | standard deviation |
|---|---|---|
| DT | 0.892 | 0.012 |
| SVM | 0.884 | 0.011 |
| KNN | 0.883 | 0.007 |

FIG.7

METHOD OF CREATING CHARACTERISTIC PEAK PROFILES OF MASS SPECTRA AND IDENTIFICATION MODEL FOR ANALYZING AND IDENTIFYING MICROORGANIZM

BACKGROUND OF THE INVENTION

1. Field of the Invention

The invention relates to a method of analyzing mass spectrometer signals and more particularly to a method of creating characteristic peak profiles of mass spectra (MS) and identification model for analyzing and identifying microorganism by analyzing the MS of their biomolecules. The characteristic spectral profile is protein expression pattern obtained by analyzing signals from matrix-assisted laser desorption/ionization time of flight mass spectrometer (MALDI-TOF MS) of microorganism isolates of an identical feature. The MALDI-TOF MS data of microorganism isolates are first processed by discretization and density-based clustering to find m/z values of spectral peaks with high probability of occurrence. The m/z values of high occurrence probability altogether forms a characteristic MS peak profile for a specific feature of microorganisms. Then, machine learning methods are used to integrate the profiles from different features of microorganisms to create classification models for analyzing and identifying those microorganisms.

2. Description of Related Art

Conventionally, technologies of using mass spectrum (MS) to identify the species of an unknown microorganism involve comparing the MS of the unknown microorganism isolate to those of known microorganisms in an isolate MS database, or comparing the isolate MS of the unknown microorganism to the characteristic MS species profiles of known microorganisms. In the approach of isolate MS database comparison, it is required to gather all the isolate MS data of known microorganisms in a database. However, microorganisms evolve constantly. Thus, it is required to gather a huge amount of MS data of known microorganism isolates in the database. Further, in the identification step, the comparison process of the isolate MS of the unknown microorganism in the large isolate MS database of known microorganisms is time consuming. That is, a large data storage for efficient and accurate comparison is required. And in turn, complex hardware is required.

Currently, no intelligent technologies are available to efficiently analyze MALDI-TOF MS data of microorganisms for the identification of their features. Particularly, there is a signal drift problem in microorganism MALDI-TOF MS data when the MS data is acquired from different analysis batches. In this case, the database comparison approach may consume additional time and involve more comparison complexity. As a result, comparison results regarding sub-species, antibiotics resistance, or toxicology identification are not reliable.

In the profile comparison approach, only a few typical m/z values of known microorganisms are included in the species profile database. For some specific microorganisms, the identification capability of this approach is limited. It can only correctly identify their genus but not species of those microorganisms. For this reason, this approach cannot be applied to the identification of sub-species, antibiotics resistance and toxicity for microorganisms.

There is a clinical need for identifying the features of unknown microorganisms. For meeting the need, clinical support staff must perform additional time consuming tests including biochemical/metabolic tests or multiple gene sequencing for unknown microorganisms. Unfortunately, such tests involve additional cost, including man power and materials.

Thus, the need for improvement does exist.

SUMMARY OF THE INVENTION

Therefore one object of the invention is to provide a method of creating characteristic peak profile of mass spectra and identification model for analyzing and identifying microorganism by analyzing the MS of their biomolecules. The process comprises the following steps: 1) gathering MALDI-TOF MS data of microorganism isolates of the same feature; 2) discretizing the MALDI-TOF MS data of microorganism isolates; 3) using density-based clustering to find the m/z values of spectral peaks with a predetermined probability of occurrence among the microorganism isolates; 4) creating a characteristic MS peak profile from the frequently occurred m/z values altogether and naming the characteristic MS peak profile as a feature template. That is, the m/z values of peaks were aligned among the isolates. If a particular m/z value has a high probability of occurrence among the isolates of an identical feature, it is selected as a representative peak in the characteristic peak profile for that feature. Such a profile is called the feature template; 5) repeating steps 1) to 4) for microorganism isolates of every other feature to generate their feature template; 6) matching the mass spectrum of each known microorganism isolate against all the feature templates, resulting in "matched vectors". The matched vectors are then concatenated into a single "integrated vector," in which each element of the integrated vector is the m/z value of a peak corresponding to a representative peak in the feature templates; 7) using a machine learning method and the integrated vectors generated from all of the microorganism isolates to create a classification model for microorganism identification; 8) obtaining the MALDI-TOF MS data of an unknown microorganism isolate; 9) discretizing the MALDI-TOF MS data of the unknown isolate; 10) matching the discretized mass spectrum of the unknown isolate against all the feature templates to form an integrated vector; and 11) using the classification model created in the step 7) to analyze the integrated vector of the unknown microorganism isolate to identify its feature.

Preferably, the machine learning method is Support Vector Machine (SVM), Artificial Neuron Network (ANN), k Nearest Neighbor (kNN), Logistic Regression, Fuzzy Logic, Bayesian Algorithm, Decision Tree (DT), Classification And Regression Tree (CART), or any combination of SVM, ANN, kNN, Logistic Regression, Fuzzy Logic, Bayesian Algorithm, DT, and CART.

Preferably, the microorganisms are bacteria, molds, or viruses.

Preferably, the features of microorganisms are species, sub-species, resistance to antibiotics, or toxicity.

The invention has the following advantages and benefits in comparison with the conventional art:

The characteristic peak profile of this invention corresponds to the representative peaks likely common to a specific feature of microorganism. The elements of a characteristic profile are the m/z values of spectral peaks with high probability of occurrence among many isolates of an identical feature. That is, the MS signals of many isolates of an identical feature can be compressed into a single characteristic peak profile of this invention. Thus, space for storing data is greatly decreased. And in turn, subsequent data comparison and analysis operations are greatly decreased.

The number of peaks in a characteristic peak profile can be determined flexibly. Thus, both identification precision and purpose can be adjusted flexibly. For example, the identification purpose can be for microorganism species, sub-species, resistance to antibiotics, or toxicity. With the increased precision of MS data analysis, healthcare employees can use the analysis result to correctly use antibiotics for infection control in near real time.

The novel methods of this invention solve the signal drift problem in microorganism MALDI-TOF MS data when the MS data are acquired from different analysis batches. The creation of the integrated vectors facilitates the construction of microorganism identification models using machine learning methods. Machine learning methods are characterized by high accuracy, high performance and high repeatability. Thus, the analysis results of MS signals of this invention can be widely used in many applications. And in turn, it decreases the requirement of manual operation and manual intervention. Finally, it improves greatly the reduction of both man power and cost.

The above and other objects, features and advantages of the invention will become apparent from the following detailed description taken with the accompanying drawings.

BRIEF DESCRIPTION OF THE DRAWINGS

FIG. 3 shows three examples of the characteristic peak profiles of mass spectra (feature templates) according to the invention;

FIG. 4 is an integrated vector diagram according to the invention, each element of the integrated vector having a value of "0" or "1". Alternatively, log value can be used to represent the element value of the integrated vector and the log value is a derivative of signals at a specific m/z value of MS;

FIG. 6 is a table showing the average AUC and the corresponding standard deviation of identification models for MRSA sub-species ST5, ST45, ST59 and ST 239 according to the invention. The models were created by machine learning methods DT, SVM and kNN respectively; and FIG. 7 is a table showing the accuracy and the corresponding standard deviation of multiclass classification models for MRSA sub-species ST5, ST45, ST59 and ST 239 according to the invention. The models were created by machine learning methods DT, SVM and kNN respectively.

DETAILED DESCRIPTION OF THE INVENTION

Figure 1:
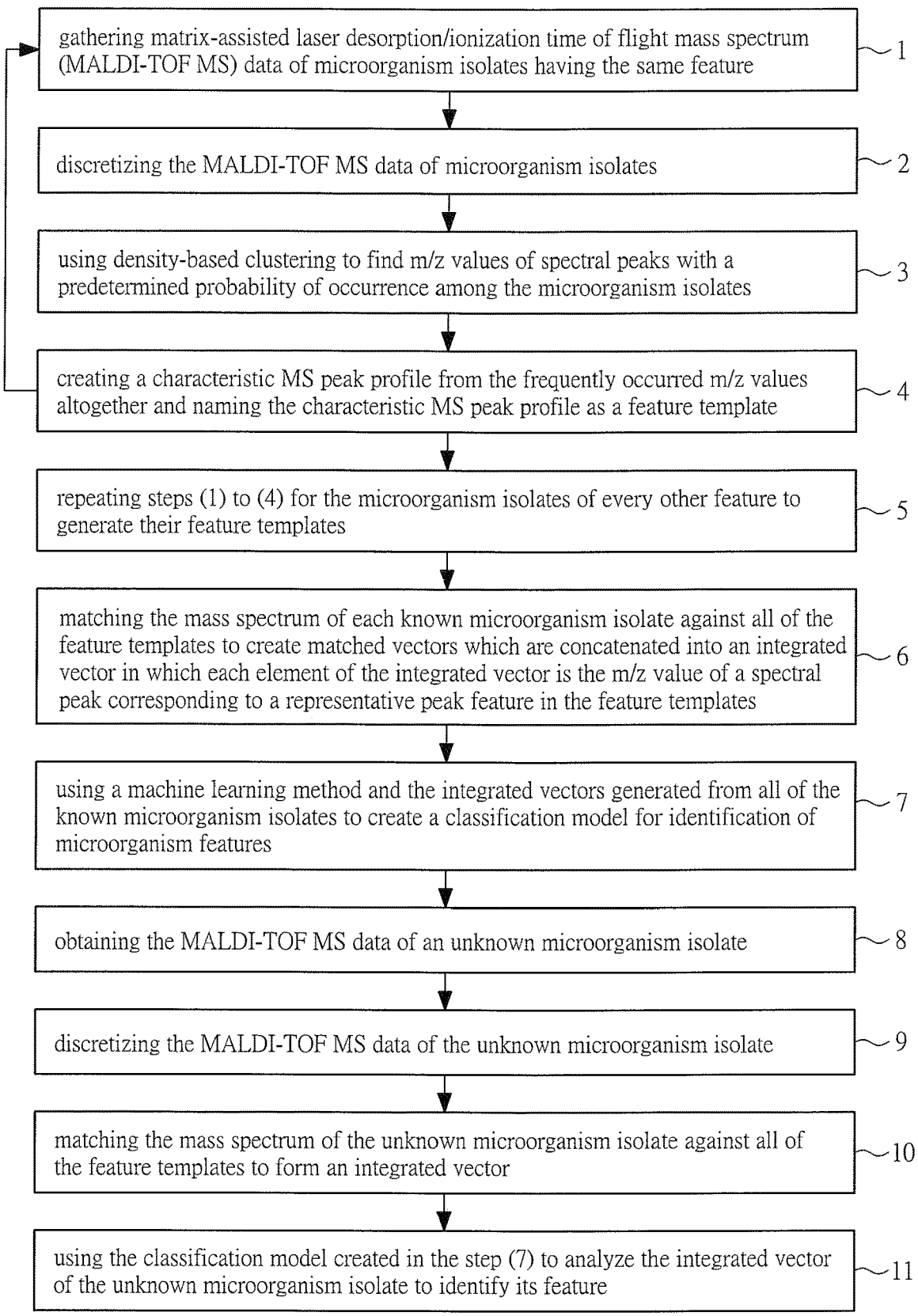
FIG. 1 is a flow chart of the method of creating a characteristic peak profile of an intelligent feature mass spectra and identification model for analyzing and identifying microorganism by analyzing the MS of their biomolecules according to the invention.

Referring to FIG. 1, a flow chart of the method of creating a characteristic peak profile of mass spectra and identification model for analyzing and identifying microorganism by analyzing the MS of their biomolecules in accordance with the invention is illustrated by the following steps:

In step 1, the MALDI-TOF MS data of microorganism isolates having the same feature is obtained.

In step 2, discretization of the data is performed;

In step 3, density-based clustering is used to find the frequently occurred m/z values of the MS peaks among the isolates;

In step 4, a characteristic MS peak profile is created from the frequently occurred m/z values altogether. Such a profile is called the feature template.

In step 5, steps 1 to 4 are repeated for microorganism isolates of every other feature to generate their feature templates.

In step 6, the mass spectrum of each known isolate is matched against all the feature templates, resulting in matched vectors. The matched vectors are then concatenated into a single "integrated vector."

In step 7, a machine learning method and the integrated vectors generated from all known isolates are used to create a classification model for the identification of microorganism feature.

In step 8, the MALDI-TOF MS data is obtained from an unknown microorganism isolate; and in step 9, discretization of the MALDI-TOF MS data of the unknown isolate is performed.

In step 10, the mass spectrum of the unknown isolate is matched against all the feature templates to obtain an integrated vector.

In step 11, the classification model is used to analyze the integrated vector of the unknown isolate to identify its feature.

Sub-species of Methicillin-Resistant *Staphylococcus aureus* (MRSA) is taken as exemplary example by the invention. MALDI-TOF MS data of 125 MRSA isolates causing bacteremia are collected. Sub-species of the MRSA isolates are identified by Multi-Locus Sequence Typing (MLST). In the invention, four sub-species such as ST5, ST45, ST59 and ST239 are included in the data.

Figure 2:
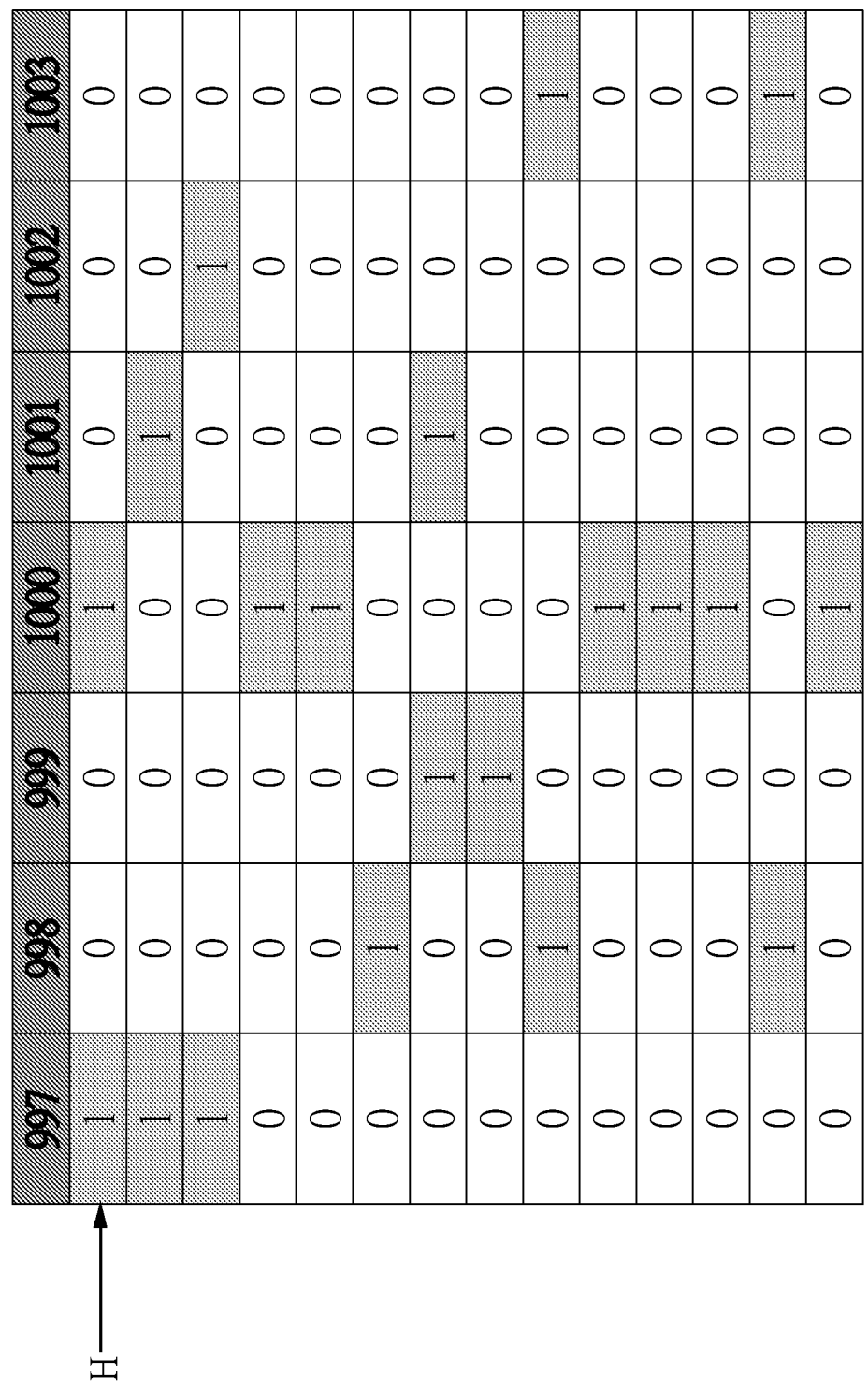
FIG. 2 is a table showing the MS data of a number of microorganism isolates and the MS data have been processed by discretization, with data at m/z value 1,000 being emphasized, each row representing the MS data of a single isolate, "1" representing strong signals at a specific m/z value, and "0" representing weak signals at a specific m/z value according to the invention.

Referring to FIGS. 2 and 3, discretization of isolate MS data of above sub-species is done, and the size of discretization interval is an m/z interval. Density-based clustering is used to find the m/z values of spectral peaks with high probability of occurrence among the isolates of an identical sub-species. FIG. 2 shows the discretized MS data examples of a number of microorganism isolates with a horizontal arrow H pointing to the first isolate. It indicates that strong signals (i.e., "1") exist at m/z values 997 and 1000 and no signal (i.e., "0") exists at m/z values 998, 1001, 1002 and 1003 for the isolate.

Likewise, in FIG. 2, discretized MS data examples of 14 isolates having the same sub-species are shown. After using the density-based clustering technique, it is found that strong signals frequently occur at m/z value 1,000 among the 14 isolates of the same sub-species. As indicated by FIG. 2, the signals of mass spectrometer may have drift problem. A molecule of m/z value 1000 may produce strong signals around m/z value 1000 (for example 999 or 1001) but not at m/z value 1000 exactly.

Parts of the characteristic MS peak profiles (feature types) of sub-species A, sub-species B and sub-species C are shown In FIG. 3 in which each row represents a characteristic peak profile of mass spectra. Regarding sub-species A, the signal peaks of its isolates occur frequently at m/z values 1276.889, 1505.849, 1934.423, 2066.205, 2081.884, 2149.891, 2241.782, 2411.518, 2428.76, 2428.983 and 2450.723. These frequently occurred m/z values are the representative peaks likely common to sub-species A. Hence, it is concluded that the frequently occurred m/z values among the isolates of an identical feature altogether represent the characteristic MS peak profile for this feature of microorganisms.

The characteristic MS peak profiles of a plurality of specific sub-species can be created by repeating steps 1 to 4 in the flow chart of FIG. 1. Such profiles are called feature templates. The mass spectrum of each known isolate is matched against all the feature templates of the selected sub-species to obtain a plurality of matched vectors. The matched vectors are then concatenated into a single integrated vector. Further, the integrated vectors of known isolates and machine learning methods are used to create classification models for sub-species identification.

Figure 5:
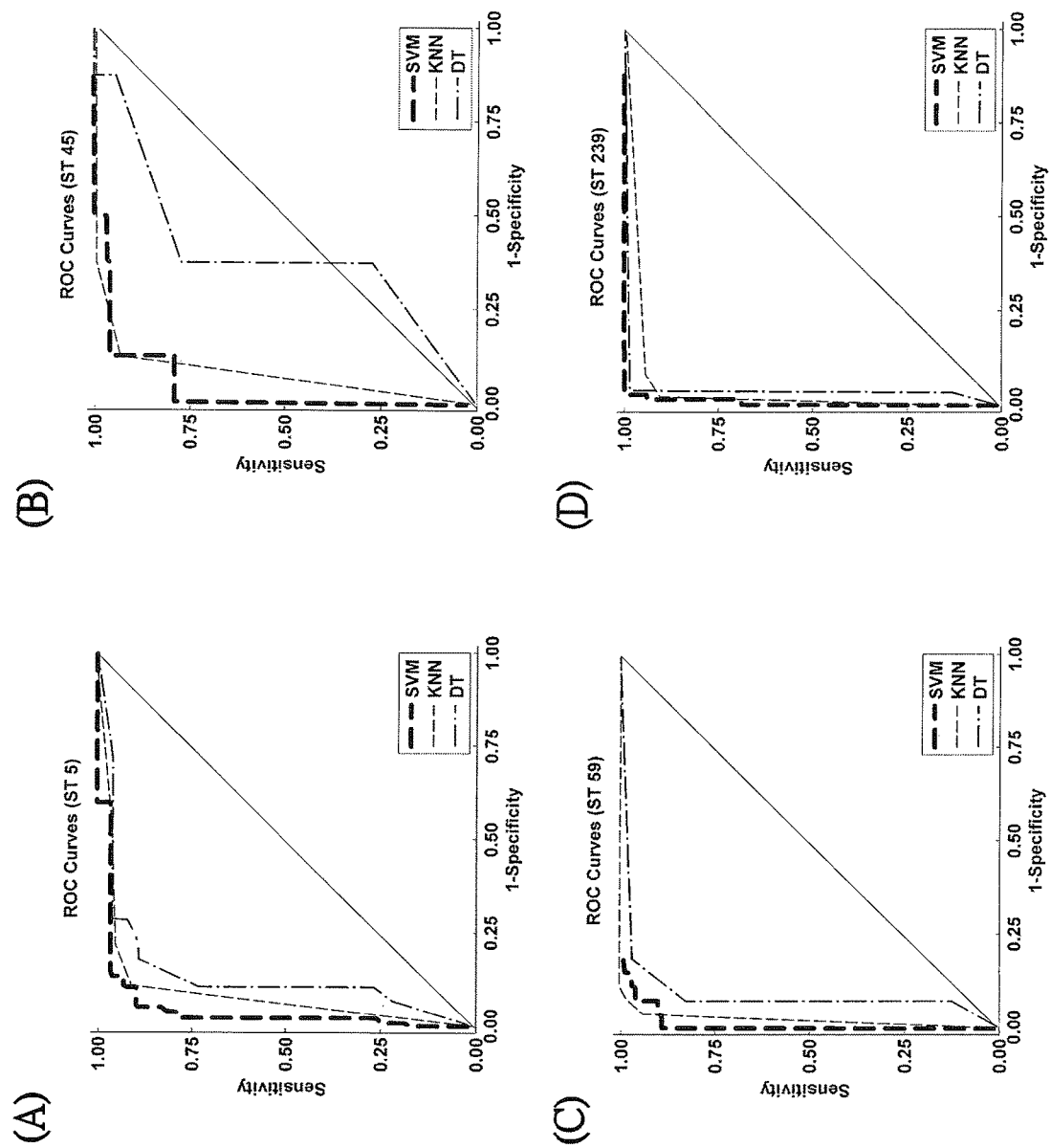
FIG. 5 shows four ROC curves based on binary identification model of MRSA sub-species according to the invention.

Referring to FIGS. 4 and 5, in the identification of an unknown isolate, its MALDI-TOF MS data is obtained first. Discretization of the MS data of the unknown isolate is performed. The discretized MS data of the unknown isolate is matched against all the feature templates of the selected sub-species including ST5, ST45, ST59 and ST239 in terms of signals to obtain a plurality of matched vectors. Each matched vector denotes how the mass spectrometer signals of the unknown isolate are similar to those of each corresponding sub-species.

As shown in FIG. 4, the discretized MS data of an unknown isolate is matched against the feature templates of sub-species A, B, and C, and three different matched vectors such as vectors 1, 2 and 3 are obtained. Take vector 1 for example, "1" represents that there is a peak match at the corresponding m/z value between the discretized MS signals of the unknown isolate and the feature template of sub-species A. To the contrary, "0" represents that there is no peak match at the corresponding m/z value. Then, vectors 1, 2 and 3 are concatenated together to create an integrated vector for the unknown isolate. In the identification problem of specific microorganisms, the size of the integrated vectors is fixed so as to facilitate the analysis and construction of microorganism identification models using machine learning methods.

Referring to FIGS. 5, 6 and 7, three different machine learning methods namely Decision Tree (DT), Support Vector Machine (SVM) and k Nearest Neighbor (kNN) are used in the embodiment. In FIG. 5, binary identification models are created for each sub-species and they have good performance in terms of ROC curves. FIG. 6 shows that AUCs (i.e., area under Receiver Operating Characteristic (ROC) curve) of binary identification models for ST5 are in the range of 0.86 and 0.95 and those for ST45, ST59 and ST239 are most about 0.95. FIG. 7 shows the performance of multi-class identification models for multiple sub-species. The multi-class identification models are different from the binary identification models in that the former can identify multiple sub-species at one time. That is, an isolate belonging to sub-species ST5, ST45, ST59 or ST239 can be identified by only one multi-class identification model. It is concluded that the sub-species identification models created by the machine learning methods had good performance and achieved accuracy about 90%. Further, the standard deviation of the model accuracy achieved by each of DT, SVM and kNN is very small and it means that the identification models created by the machine learning methods have high accuracy consistently.

It is envisaged by the method of the invention that high accuracy of sub-species identification can be done by the classification models created by machine learning methods. Further, sub-species identification is one of the applications in identification of microorganism features. In other words, the method of this invention can be easily extended to the identification of species, sub-species, resistance to antibiotics, or toxicity.

While the invention has been described in terms of preferred embodiments, those skilled in the art will recognize that the invention can be practiced with modifications within the spirit and scope of the appended claims.

What is claimed is:

1. A method of creating characteristic peak profiles of mass spectra and identification model for analyzing and identifying microorganisms by analyzing the mass spectra of their biomolecules, the method comprising the steps of:
    (1) gathering matrix-assisted laser desorption/ionization time of flight mass spectrum (MALDI-TOF MS) data of microorganism isolates having a same feature;
    (2) discretizing the MALDI-TOF MS data of the microorganism isolates;
    (3) using density-based clustering to find m/z (mass to charge) values of spectral peaks with a predetermined probability of occurrence among the microorganism isolates;
    (4) creating a characteristic MS peak profile from frequently occurred m/z values altogether and naming the characteristic MS peak profile as a feature template;
    (5) repeating steps (1) to (4) for the microorganism isolates of every other feature to generate their feature templates;
    (6) matching the mass spectrum of each known microorganism isolate against all of the feature templates to create matched vectors which are concatenated into an integrated vector in which each element of the integrated vector is the m/z value of a spectral peak corresponding to a representative peak feature in the feature templates;
    (7) using a machine learning method and the integrated vectors generated from all of the known microorganism isolates to create a classification model for identification of microorganism features;
    (8) obtaining the MALDI-TOF MS data of an unknown microorganism isolate;
    (9) discretizing the MALDI-TOF MS data of the unknown microorganism isolate;
    (10) matching the mass spectrum of the unknown microorganism isolate against all of the feature templates to form an integrated vector of the unknown microorganism isolate; and
    (11) using the classification model created in the step (7) to analyze the integrated vector of the unknown microorganism isolate to identify its feature.

2. The method of claim 1, wherein the machine learning method is Support Vector Machine (SVM), Artificial Neuron Network (ANN), k Nearest Neighbor (kNN), Logistic Regression, Fuzzy Logic, Bayesian Algorithms, Decision Tree Induction Algorithm (DT), Classification And Regression Tree (CART), or any combination of SVM, ANN, kNN, Logistic Regression, Fuzzy Logic, Bayesian Algorithms, DT, and CART.

3. The method of claim 1, wherein the microorganisms are bacteria, molds, or viruses.

4. The method of claim 1, wherein the features of microorganisms are species, sub-species, resistance to antibiotics, or toxicity.

\* \* \* \* \*